US006737645B2

(12) United States Patent
Foster et al.

(10) Patent No.: US 6,737,645 B2
(45) Date of Patent: May 18, 2004

(54) METHOD FOR QUALIFYING BOTTLE RINSER

(75) Inventors: Tammy Foster, Sarasota, FL (US); Christine Jansen, St. Petersburg, FL (US); James D. Schuman, Bradenton, FL (US)

(73) Assignee: Tropicana Products, Inc.

( * ) Notice: Subject to any disclaimer, the term of this patent is extended or adjusted under 35 U.S.C. 154(b) by 83 days.

(21) Appl. No.: 10/233,077

(22) Filed: Aug. 30, 2002

(65) Prior Publication Data

US 2004/0040860 A1 Mar. 4, 2004

(51) Int. Cl.[7] ............................................. G01N 21/64
(52) U.S. Cl. ..................................... 250/302; 250/458.1
(58) Field of Search ........................... 250/458.1, 459.1, 250/461.1, 302

(56) References Cited

U.S. PATENT DOCUMENTS

| | | |
|---|---|---|
| 1,584,022 A | 5/1926 | Englund |
| 2,127,548 A | 8/1938 | Boyle et al. |
| 2,254,609 A | 9/1941 | Kinzer |
| 2,416,619 A | 2/1947 | Fleisher |
| 2,472,522 A | 6/1949 | Taber |
| 2,479,743 A | 8/1949 | Hall et al. |
| 3,190,724 A | 6/1965 | Compton et al. |
| 3,386,920 A | 6/1968 | Alburger |
| 3,422,670 A | 1/1969 | Alburger |
| 3,558,505 A | 1/1971 | Milot-Fijalkowski |
| 3,627,469 A | 12/1971 | Cheng |
| 3,676,007 A | 7/1972 | Kiess |
| 3,748,469 A | 7/1973 | Molina |
| 3,803,051 A | 4/1974 | Molina |
| 3,912,653 A | 10/1975 | Alburger |
| 4,273,671 A | 6/1981 | Allinikov |
| 4,300,689 A | 11/1981 | Franklin et al. |
| 4,331,871 A | 5/1982 | Allinikov |
| 4,382,679 A | 5/1983 | Lee |
| 4,392,982 A | 7/1983 | Molina |
| 4,407,842 A | 10/1983 | Shepard |
| 4,407,960 A | 10/1983 | Tratnyek |
| 4,448,548 A | 5/1984 | Foley |
| 4,641,518 A | 2/1987 | Hutchings |
| 4,678,658 A | 7/1987 | Casey et al. |
| 4,743,398 A | 5/1988 | Brown et al. |
| 4,756,854 A | 7/1988 | Wegrzyn |
| 4,778,999 A * | 10/1988 | Fisher ...................... 250/461.1 |
| 4,830,192 A | 5/1989 | Plester et al. |
| 4,847,066 A | 7/1989 | Honigs et al. |
| 4,858,465 A | 8/1989 | Molina |
| 4,863,627 A | 9/1989 | Davies et al. |
| 4,896,478 A * | 1/1990 | Reiter .......................... 53/426 |
| 5,057,303 A | 10/1991 | Casey |
| 5,063,297 A * | 11/1991 | Hardenbrook et al. ... 250/458.1 |
| 5,067,616 A | 11/1991 | Plester et al. |
| 5,110,492 A | 5/1992 | Casey |
| 5,123,261 A | 6/1992 | Cope |
| RE34,515 E | 1/1994 | Foley |
| 5,416,323 A | 5/1995 | Hoots et al. |
| 5,578,240 A | 11/1996 | Park et al. |
| 5,658,798 A | 8/1997 | Bertin et al. |
| 5,670,469 A | 9/1997 | Dingus et al. |
| 5,703,024 A | 12/1997 | Park et al. |
| 5,832,697 A | 11/1998 | Rogers |
| 5,843,374 A * | 12/1998 | Sizer et al. ................... 422/24 |
| 5,900,067 A | 5/1999 | Jones |
| 5,955,025 A | 9/1999 | Barrett |
| 6,087,179 A | 7/2000 | Beriozkina et al. |
| 6,135,015 A | 10/2000 | Mendez |
| 6,193,931 B1 * | 2/2001 | Lin et al. ....................... 422/28 |

* cited by examiner

*Primary Examiner*—Constantine Hannaher
*Assistant Examiner*—Timothy Moran
(74) *Attorney, Agent, or Firm*—Cook, Alex, McFarron Manzo, Cummings & Mehler, Ltd.

(57) ABSTRACT

A method for determining whether effective coverage of the interior of a bottle with a sprayed sanitizer in a bottle fill-and-cap operation is attained by using a fluorescing solution, preferably comprising riboflavin and sucrose dissolved in water, that is sprayed on the interior of the bottle by the same spray system by which the sanitizer is sprayed. After application of the fluorescing solution, UV light is applied to the bottle interior to activate the fluorescing solution and thus make evident the spray pattern. Spray pattern adjustments can be made as needed, in order to be certain that the entirety of the inside surface of the bottle is coated. Once the spray pattern is thus set, the equipment is qualified to be used for production, with the sanitizer being sprayed according to the same spray pattern.

12 Claims, No Drawings

METHOD FOR QUALIFYING BOTTLE RINSER

BACKGROUND OF THE INVENTION

Various food and other substances subject to spoilage and/or contamination are commonly packaged in bottles in a fill-and-seal operation. Because of the desire for greater purity and longer shelf life for such bottled products, a sanitizer, such as a peroxide ($H_2O_2$), is often sprayed on the interior of the bottle prior to filling to reduce the likelihood of product contamination or spoilage due to microorganisms. As can be readily appreciated, the effectiveness of the sanitizer depends on thorough coverage of the interior of the container by the sanitizer spray. The sub-system for spraying the sanitizer has several operating parameters which can be varied to change the effectiveness of the spray coverage, such as the spray pattern, system operating pressure, sanitizer flow rate, temperature, sanitizer concentration, contact time, and the like. With respect to the spray pattern of the sanitizer, this is primarily a function of the configuration and direction of the nozzles through which the sanitizer is sprayed. However, once these parameters have been established and the sanitizing function for the production line qualified, effective sanitizer coverage is reasonably assured.

Accordingly, it is an object of the present invention to provide a method for determining the effectiveness of a sanitizer spray sub-system in a bottle filling and capping procedure.

More specifically, it is an object of the present invention to provide a method for visually determining the degree of spray coverage for a bottle sanitizer so that the optimal operating characteristics for the nozzles of the spray system may be established and maintained during on-line bottle filling and capping operations.

SUMMARY OF THE INVENTION

These objects, as well as others that will become apparent upon reference to the following detailed description, are provided by a method for evaluating the degree of coverage of a spray on the interior of a container in which a fluorescing solution or dye is prepared and applied to the interior of the container through the nozzles used in the fill-and-cap line to apply spray sanitizer. The fluorescing dye is then dried, or allowed to dry, on the interior of the container, after which the interior of the container is illuminated with UV light to activate the fluorescing dye. The activated fluorescing dye is viewed and evaluated to provide an indication of the extent of spray coverage based upon the degree or percentage of surface area emitting light and the intensity of light cast by the activated fluorescing dye.

Preferably, the fluorescing dye comprises a riboflavin, combined with sucrose and water. In addition, after the activated fluorescing dye is viewed and coverage evaluated, the nozzles may be adjusted and the steps repeated until it is determined that satisfactory coverage from the spray is attained.

DETAILED DESCRIPTION OF THE PREFERRED EMBODIMENT

Fill-and-seal or fill-and-cap bottling operations are well known in the art and, consequently, are not discussed in detail herein. A sub-system commonly forming a part of such an operation is a spray system, including nozzles, through which a sanitizing rinse is sprayed onto the interior surfaces of the bottles or containers to be filled. Such bottle rinser systems, when initially started-up or restarted after a shut-down, need to be qualified with the various parameters established before the operation is used for production.

In keeping with the present invention, a method is provided for qualifying a bottle rinser sub-system of a bottle fill-and-seal operation by providing a way by which it can be determined whether the interiors of the bottles are adequately covered by the spray emitted by the sanitizer spray sub-system.

In general, a fluorescing solution or dye is sprayed onto the interior of bottles, allowed to dry, and then exposed to UV light, which will cause the dried dye to emit light. The interior of the bottle is subjected to a visual inspection and an assessment is made as to whether the coverage is satisfactory based upon, e.g., whether the entire surface emits light, indicating that the spray reached the entire interior of the bottle and whether the light is of even intensity, indicating an even coverage of the spray. If the coverage is satisfactory, no changes to the spray sub-system are indicated. However, if coverage is unsatisfactory, the spray nozzles may be adjusted and the test repeated, until satisfactory coverage is attained. Once satisfactory coverage is attained, the sanitizing function of the bottling operation is qualified to go into production.

The method is applicable to any translucent or transparent packaging material, such as HDPE, PET, glass, and the like, which transmit UV light needed to act the fluorescing dye. The term translucent is understood to include materials through which adequate light is transmitted, from relatively clear or transparent materials to ones which boarder on opaque.

A preferred fluorescing dye is made from riboflavin, which is Vitamin $B_{12}$. The riboflavin is extremely sensitive to light and has an intense greenish yellow fluorescence when exposed to UV light. The riboflavin is added to water, along with sucrose, which is added to provide for adhesion. An example of a formula for a fluorescing dye for use in the present invention is set forth in

TABLE I

| FLUORESCING DYE | |
|---|---|
| Water | 1 liter |
| Riboflavin | 0.2 gram |
| Sucrose | 100 grams |

The riboflavin may be a commercially-available reagent grade product, such as Eastman Kodak #EK1177112 Riboflavin Orange Powder, or an equivalent. The water may be plant or process water.

The fluorescing solution is added to the sanitizer pump system after the sanitizer has been removed and the sanitizer system flushed. The sanitizer system is then primed with the fluorescing solution and the processing parameters set.

After the solution is sprayed onto the interiors of the test bottles, the solution is allowed to dry. This may be done by circulating ambient air into the interiors of the bottles for between approximately 3 to 7 seconds.

The interiors of the bottles are then illuminated with UV light, preferably from a long-wave UV lamp, to activate the riboflavin. The translucent nature of the bottles or containers allows the fluorescing dye to be activated by shining the UV light through the walls of the bottle or container. Appropriately qualified personnel then view the illuminated interior of the bottle to evaluate the degree of both the completeness of coverage (i.e., the percentage of the surface area that emits light) and the evenness of the coverage (i.e., whether the light emitted by the activated dye is of the same intensity over the entire coated surface). These determinations can be made by the unaided eye. If coverage is incomplete and/or uneven, the spray nozzles can be adjusted to improve these parameters. The test is then repeated to evaluate the effectiveness of the changed nozzle settings. Once it is determined that the coverage is satisfactory, the qualification of the sanitary spray sub-system nozzle settings is complete.

Thus, a method for evaluating the effectiveness of the coverage of the sanitizing spray in a bottle fill-and-cap operation has been provided that meets all of the objects of present invention. Although the invention has been described in terms of a preferred embodiment, there is no intent to limit it to the same. Instead, the invention is defined by the scope of the following claims.

What is claimed:

1. In a bottle fill-and-capping operation for translucent containers in which the interiors of the containers are sprayed with a sanitizing solution prior to filling, the sanitizing spray being applied through one or more nozzles, a method for evaluating the effectiveness of the coverage of sanitizing solution comprising:

A) preparing a fluorescing solution;
   B) applying the fluorescing solution to the interior of one or more translucent containers through the one or more nozzles used to spray sanitizing solution;
   C) allowing the fluorescing solution to dry;
   D) illuminating the interiors of the containers with an UV light to activate the fluorescing solution;
   E) viewing the activated fluorescing solution; and
   F) evaluating the extent of spray coverage based upon the light cast by the activated fluorescing solution.

2. The method of claim 1 further comprising:
   G) adjusting the one or more nozzles used to spray the sanitizing solution; and
   H) repeating steps B–F, and as necessary step G, until satisfactory coverage is attained.

3. The method of claim 1 wherein the fluorescing solution comprises riboflavin, sucrose and water.

4. The method of claim 3 wherein the fluorescing solution comprises approximately 0.2 g riboflavin and 100 g sucrose for each liter of water.

5. The method of claim 1 wherein the drying is accomplished by circulation of ambient air into the interiors of the containers.

6. The method of claim 1 wherein the UV light is provided by a long-wave UV lamp.

7. In a bottle fill-and-capping operation for translucent containers in which the interiors of the containers are contacted with a sanitizing solution prior to filling, a method for evaluating the effectiveness of the coverage of sanitizing solution comprising:

A) preparing a fluorescing solution;
   B) applying the fluorescing solution to the interior of one or more translucent containers by directing the sanitizing solution onto the interior;
   C) allowing the fluorescing solution to dry;
   D) illuminating the interiors of the containers with an UV light to activate the fluorescing solution;
   E) viewing the activated fluorescing solution; and
   F) evaluating the extent of sanitizing solution coverage based upon the light cast by the activated fluorescing solution.

8. The method of claim 7 further comprising:
   G) adjusting the directing of the sanitizing solution; and
   H) repeating steps B–F, and as necessary step G, until satisfactory coverage is attained.

9. The method of claim 7 wherein the fluorescing solution comprises riboflavin, sucrose and water.

10. The method of claim 9 wherein the fluorescing solution comprises approximately 0.2 g riboflavin and 100 g sucrose for each liter of water.

11. The method of claim 7 wherein the drying is accomplished by circulation of ambient air into the interiors of the containers.

12. The method of claim 7 wherein the UV light is provided by a long-wave UV lamp.

* * * * *